United States Patent [19]

Cieszyński

[11] 4,078,267

[45] Mar. 14, 1978

[54] ARTIFICIAL HEART PROPELLED BY RESPIRATORY MUSCLES

[75] Inventor: Tomasz Cieszyński, Wroclaw, Poland

[73] Assignee: Akademia Medyczna, Wroclaw, Poland

[21] Appl. No.: 752,837

[22] Filed: Dec. 21, 1976

[30] Foreign Application Priority Data

Dec. 31, 1975 Poland .................................. 186268

[51] Int. Cl.² .............................................. A61F 1/24
[52] U.S. Cl. ...................................................... 3/1.7
[58] Field of Search ......... 3/1.7, 1; 128/1 D, DIG. 3, 128/214 R

[56] References Cited

U.S. PATENT DOCUMENTS

| 3,518,702 | 7/1970 | LaRussa | 3/1.7 |
|---|---|---|---|
| 3,733,616 | 5/1973 | Willis | 3/1.7 |
| 3,771,173 | 11/1973 | Lamb | 3/1.7 |
| 3,874,002 | 4/1975 | Kurpanek | 3/1.7 |

OTHER PUBLICATIONS

"A Small Ventricle-Type Pump for Prolonged Perfusions: Construction and Initial Studies, Including Attempts to Power a Pump Biologically with Skeletal Muscle", by B. Kusserow et al., Transactions A.S.A.I.O., vol. X, 1964, pp. 74–78.

"Heparin-Bearing Surfaces and Liquid Surfaces in Relation to Blood Coagulation", by L. Fourt et al., Transactions A.S.A.I.O., vol. XII, 1966, pp. 155–165.

Primary Examiner—Ronald L. Frinks
Attorney, Agent, or Firm—Haseltine, Lake & Waters

[57] ABSTRACT

An artificial heart comprising two ventricles (8) and two atria (9) adapted for inclusion in a blood circulation system via valves (17), to operate in the same manner as a live heart. The heart comprises a rigid housing (1) containing in its top part two inlet ports (2) and two outlet ports (3). Elastic ventricle (8) and elastic atrium (9) constitute a symmetrical half of the heart. The bottom part of housing (1) is shaped in the form of two parallel cylinders (4) capped tightly and slidably with buckets (5) having convex bottoms, these bottoms forming pistons (6). An elastic movable diaphragm (7) is located above each piston (6), and is circumferentially attached to the inside of cylinder (4) and to the elastic ventricle (8). Physiological liquid is contained between ventricle (8) and diaphragm (7). The top part of housing (1) is connected with a branched shank designed for attachment to the human skeleton, and buckets (5) are attached to the branched elastic, membranaceous and pedate bearer designed to rest against respiratory muscles and their bony lining. The volume of ventricles (8) and of atria (9) is about four times larger in comparison with that of a live heart. The heart is actuated by the motion of respiratory muscles which exert a pressure on buckets (5) via the bearer, the operation of the heart being similar to that of a hydraulic diaphragm-piston pump.

16 Claims, 3 Drawing Figures

ARTIFICIAL HEART PROPELLED BY RESPIRATORY MUSCLES

FIELD OF THE INVENTION

This invention relates to an artificial heart propelled by respiratory muscles, predominantly by the diaphragm, the heart being designed for implantation into a living human organism in replacement of its own insufficient heart, irreversibly afflicted by lesion.

BACKGROUND

Disclosed in U.S. Pat. No. 3,874,002 is a magneto-propelled artificial heart composed of two identical rigid housings. An inlet and an outlet port with two-element valves are provided in the top part of each housing. The top part of the housing, through which the blood flows, contains two identical spaces separated from one another by a vertical and rigid septum. A one-piece magnetic valve is provided between these spaces, one space serving the role of the atrium, the other that of the ventricle, this valve being pivotably attached to the top part of the housing, the bottom edge of this valve being against the top edge of the vertical septum. The bottom part of the housing, where a hydraulic pump is contained, is separated from the top part, through which the blood flows, by two elastic bags, these bags being attached at one end to the inner surface of the housing walls, and to the top part of the vertical septum at their other end. The bottom section of the vertical septum is flared, and a rigid partition is attached to this septum, this partition being horizontal in its mid section and bent at its sides, both ends of this partition being fixed inside the housing. There are ports provided in the bent faces of this rigid partition. A chamber with an anti-magnetic screen is contained in the bottom part of the housing, this chamber being filled with liquid, a part of this chamber constituting a pumping cylinder. The heart propulsion mechanism is contained in this chamber, this mechanism being composed of a vertically positioned ferromagnetic piston, the excitation winding of this piston being powered by batteries attached to the housing. This piston is slidably and elastically mounted on two guiding rods, the ends of said rods being fixed to two permanent magnets arranged in parallel to the ferromagnetic piston at both its sides, the poles of the magnets being disposed in opposition one to the other. The length of the moving zone of the ferromagnetic piston is the same as that of the horizontal and non-perforated section of the bottom partition. The valves are made in the form of two-arm magnetic levers swiveling on brackets mounted inside the housing, the longer arms of levers facing a recess in the wall in which two permanent magnets are installed; one magnet which is of opposite polarity to the valve pole is installed at the blood outlet side near the valve edge, the other magnet which is of the same polarity as the jointly operating pole of the valve is installed at the blood inlet side, on the extension of the axis of rotation.

The ferromagnetic piston moves in the pumping cylinder, in the space filled with liquid, in reciprocity with the changeover of the polarity of its excitation winding and due to the attraction force of both permanent magnets whose poles are opposed. This motion causes the liquid to flow, once through one and then through the other set of ports provided in the horizontal rigid partition, and from the chamber space to the space below the elastic bags, these bags causing, after being displaced upward by the liquid, that blood is forced out once from the atrium to the ventricle through the one-piece valve, and then from the ventricle to the blood circulation system, with blood being simultaneously drawn into the atrium. The valves are actuated by the jointly operating permanent magnets, they open under the pressure of flowing blood which causes the force of both opposite poles to be overcomed, these opposed poles cooperating one with the other when the valves are closed, the valves opening under the effect of repulsion of the opposed poles, the pressure of inflowing blood dropping simultaneously.

A disadvantage of the above described artificial heart is the limited capacity of the batteries which is insufficient for a permanent operation of the heart. Thus the need arises to supply the heart with voltage from external sources, this presenting another disadvantage since the winding has to be supplied with a large current required to overcome the resistance in the hydraulic pump. The principal disadvantage inherent in an external power supply for the artificial heart is the danger of infection along the power leads, this presenting a lethal danger for the person carrying such a heart. Additionally, the heart of this type requires an extra analytical and controlling apparatus to control its operation in accordance with biochemical and physical information obtained as to the health condition of the person carrying the heart.

SUMMARY OF THE INVENTION

This invention relates to an artificial heart propelled by respiratory muscles, said heart consisting of two verticles and two atria. The heart is designed for inclusion in the blood circulation system via closing and opening valves, one ventricle and one atrium of this heart, interconnected by a port with a valve opening at the side of the atrium, constituting one half of the heart, this half being separated from the other half. The essential feature of this invention is the construction wherein the heart comprises a rigid housing with a vaulted top part permanently connected with a branched shank and containing elements adjoining the atria and ventricles of the heart, and two inlet and two ports, the bottom part of this housing being shaped in the form of two cylinders situated one beside the other and slidably and tightly capped with two buckets bottomed convexely towards the inside, said buckets constituting the hollow pistons of the heart, said pistons being filled with carbon dioxide, The buckets are attached to a branched elastic membranaceous and pedate bearer, said bearer being adapted to rest against respiratory muscles and their bony lining. An elastic movable diaphragm is situated above each piston, said diaphragm being circumferentially attached to the inner surface of the cylinder and also circumferentially to the outer surface of an elastic ventricle, said ventricle having two ports coinciding with an outlet port in the housing and with a port provided in a rigid septum separating the ventricle space from that of the atrium. A physiological liquid isotonic relative to the blood and with an addition of known antithrombotic substances is contained in the space between the movable diaphragm and the elastic part of the ventricle, said movable diaphragm being connected with the said elastic part of the ventricle. Contained in the space between the piston and movable diaphragm is a liquid whose density and viscosity is less than those of water. There are two ports in the elastic atrium, said elastic atrium being terminated at the top with the housing and at the bottom with the rigid septum, said ports coinciding with an inlet port in the housing and with a port connecting the atrium with the ventricle. A pneumatic space contained between the elastic atrium, the housing elements confining the atrium, and the septum is filled with carbon dioxide. The volume of the ventricle and the atrium is about four times larger than that of an average live heart.

The basic advantage gainded from the artificial heart of the invention is, in comparison with other constructions known in the state of art, that it neither requires a separate power source nor any mechanical connections between the user and a power source. In consequence there is no danger of external infection through an incision after it is healed. This advantage has been obtained because the artificial heart of the invention is biologically powered by the user himself, namely by the respiratory muscles. This heart does not require any artificial system controlling its operation since it is automatically controlled by the central nervous system through its respiratory center. The output of the artificial heart is governed by the depth and frequency of the breathing of the user, thus protecting this person in situations of an increased activity, e.g. at an increased walking pace, when ascending stairs, during short running or other more intensive exertion, because a deeper and more frequent breathing results in an increased output of the artificial heart. The volume of the artificial heart ventricles and atria is about four times larger than that of the ventricles and atria of a live heart, because the physiological ratio of breath frequency to the beat of the heart is about 1 to 4; thus a proper blood circulation is obtained suitably to the slow rhythm of the artificial heart operation. A smaller thickness of the walls of the artificial heart as compared with that of a live heart causes the overall dimensions of the artificial heart not to be markedly increased over that of a live heart in spite of the larger volume of the artificial heart. Slightly larger overall dimensions have in practice no negative effects; and ineffective heart replaced by the artificial heart is patologically enlarged. The operation of the artificial heart is biologically controlled by the brain and the spinal bulb where the blood composition analyzers are located, these analyzers causing feedback signals to be sent out to operate respiratory muscles and thus the natural feedback is utilized to power the artificial heart.

BRIEF DESCRIPTION OF THE DRAWING

An embodiment of the present invention will now be described by way of example and with reference to the accompanying drawing in which.

DETAILED DESCRIPTION

Figure 1:
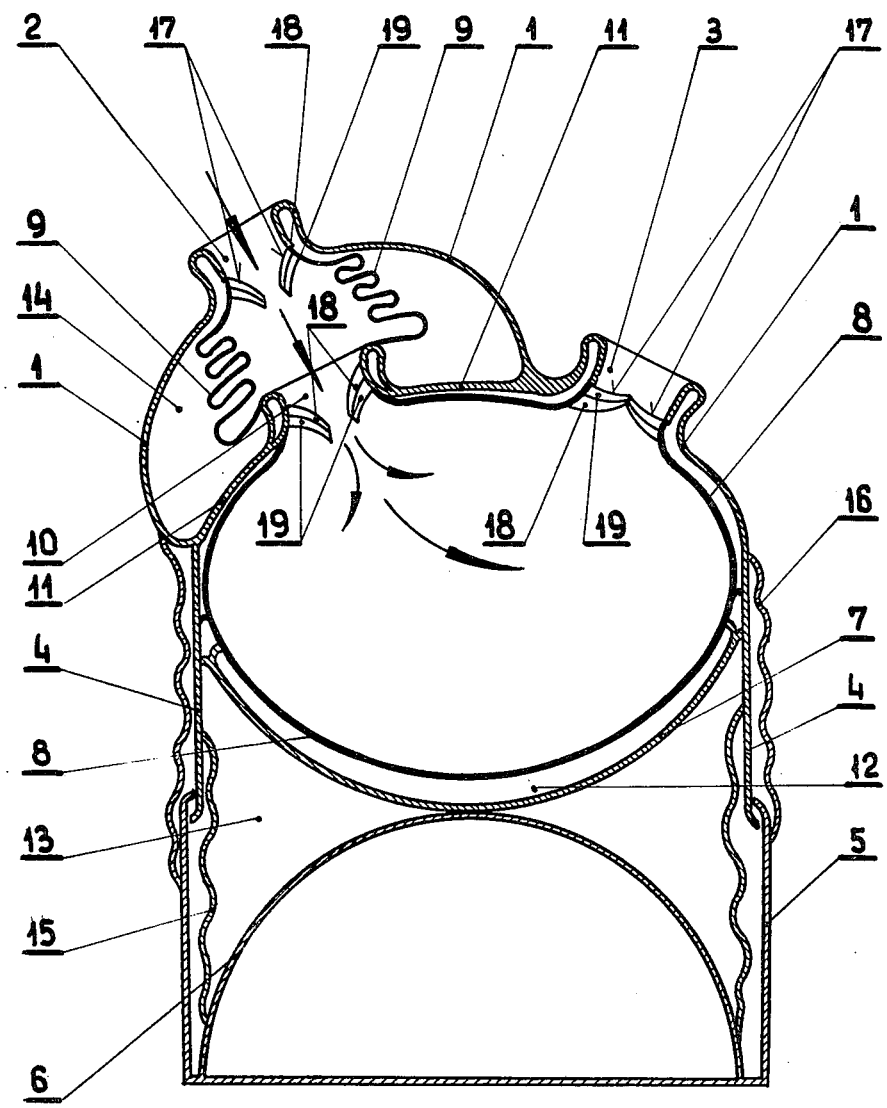
FIG. 1 illustrates one half of the artificial heart according to the invention in longitudinal section, in the expansion phase of the ventricle.
Figure 2:
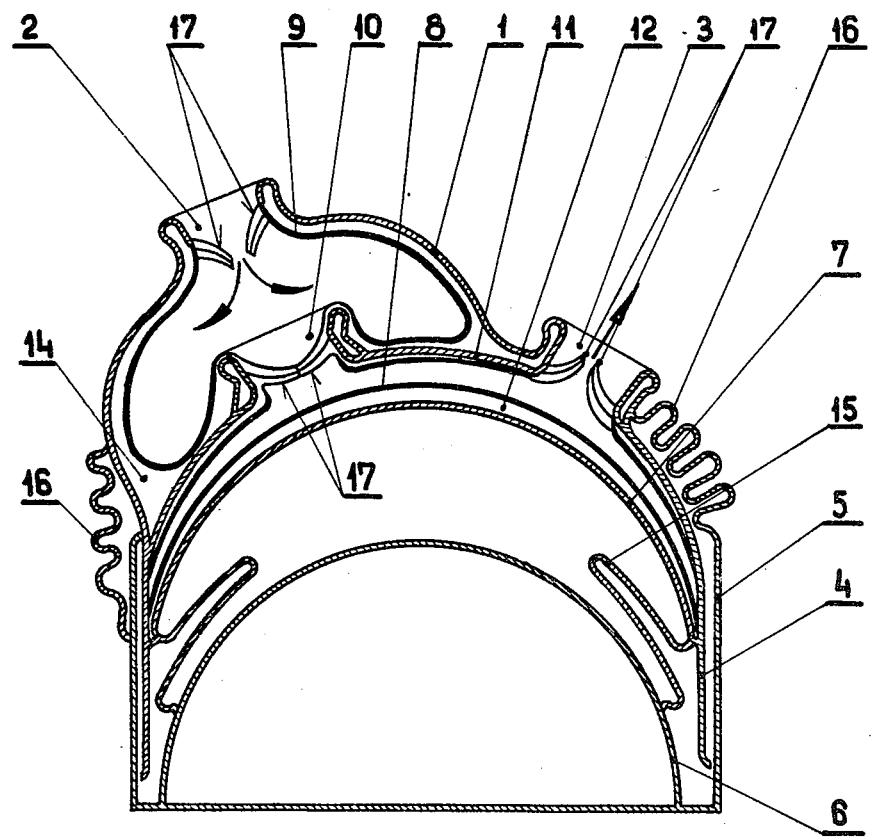
FIG. 2 illustrates the same half of the heart in the contraction phase of the ventricle.
Figure 3:
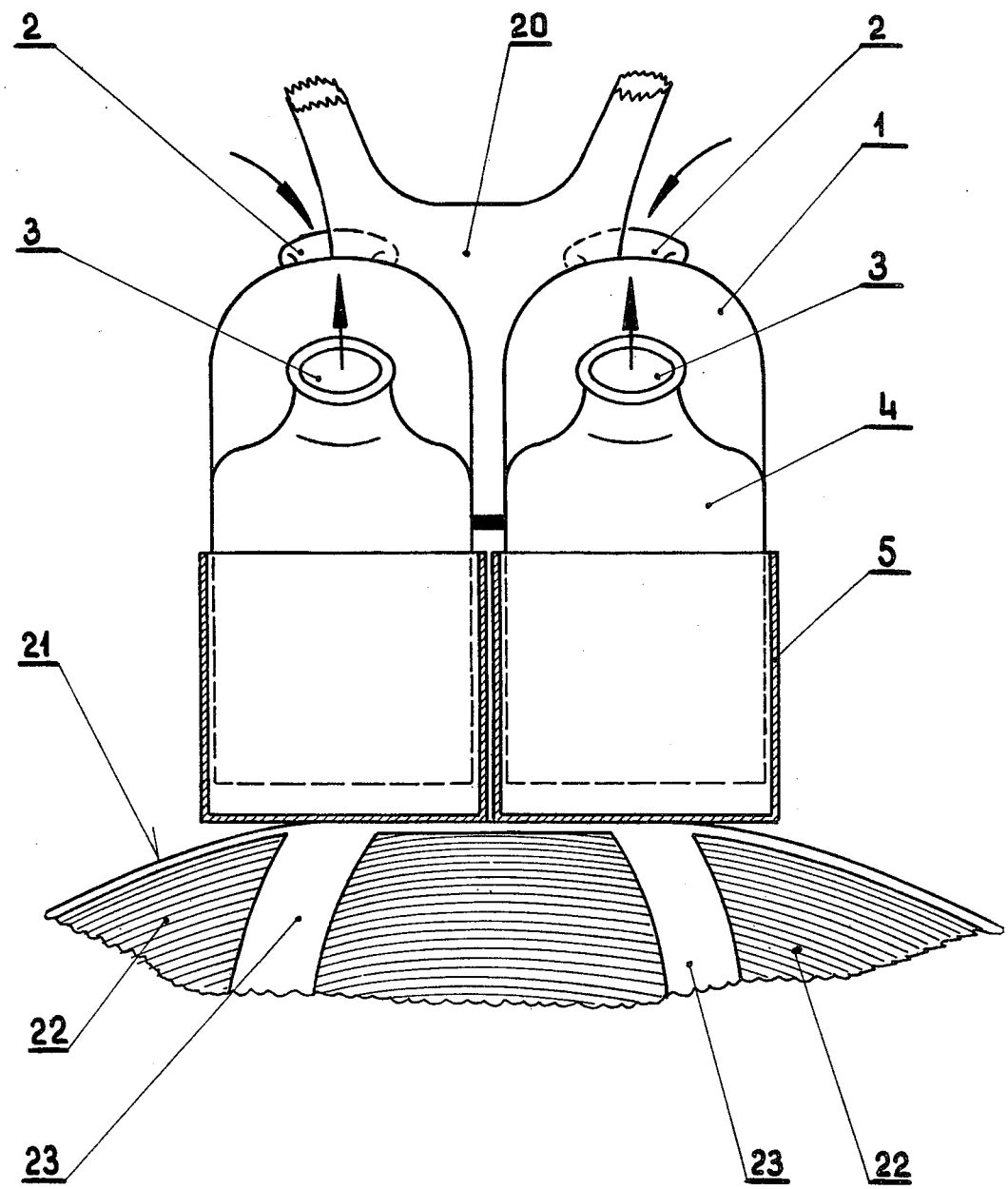
FIG. 3 is an axonometric view the heart housing supported on the user.

The embodiment of the invention illustrates an artificial heart consisting of two separate halves whose interiors are enclosed by a rigid housing 1, with two inlet ports 2 and two outlet ports 3 provided in the top and vaulted part of the said housing. Ports 2 and 3 of the left half of the heart are designed to be connected with the aorta and with the pulmonary veins to maintain the general circulation in the system of the person carrying the heart, while ports 2 and 3 of the right half of the heart are designed to be connected with both caval veins and with the pulmonary artery to maintain the lesser circulation, in the same way as in a live heart. Housing 1 is made of an epoxy resin bonded fibre glass. The bottom part of the housing is shaped in the form of two cylinders 4 situated one beside the other, said cylinders being capped with two buckets 5. The edges of buckets 5 and of cylinders 4 are flanged thus preventing disconnection of these two elements after bucket 5 reaches its extreme position of its downward travel. Buckets 5 are provided with convex bottoms 6, these bottoms constituting pistons of the heart. The pistons are hollow in order to reduce their weight and they are filled with carbon dioxide to protect the organism of the user against irreversible gas embolism in the case of a leak. An elastic movable diaphragm 7 is located above each piston 6, said diaphragm being circumferentially attached to the inner surface of bucket 5. In the top part of the housing, in its mid section, there are elastic ventricles 8 whose upper parts are rigidly attached to the housing while their lower parts are elastically deformable and which are ovoid in their expanded state, the elastic movable diaphragms 7 being also circumferentially attached to the said ventricles, said diaphragm being also attached to the respective piston 6. The top part of housing 1 encloses also an elastic atrium 9, said atrium being interconnected with ventricle 8 via port 10 provided in rigid septum 11, said septum separating the spaces of ventricle 8 and of atrium 9. Ventricle 8 and atrium 9 are made of polyurethane. An aqueous solution of physiological salt is contained in a space 12 between the movable elastic diaphragm 7 and the elastic section of ventricle 8, said elastic section being connected with the said diaphragm, said solution being isotonic relative to the blood and containing heparin, this solution protecting the life of the user in the case of a perforation at the side of ventricle 8, thus preventing the inside of the heart from becoming filled with a thrombus. A space 13 between the piston 6 and the movable elastic diaphragm 8 is filled with kerosene to obtain as low a coefficient of friction as possible since the coefficient of viscosity of kerosene is lower than that of water, also, the weight of the artificial heart is reduced since the density of kerosene is lower than that of water. There are two ports in the ventricle 8, said ports coinciding with the outlet port 3 in the housing and with the port 10 in the rigid septum. Two ports in the elastic atrium 9 coincide with the inlet port 2 in housing 1 and with port 10 connecting the ventricle 8 with atrium 9. Carbon dioxide is contained in a pneumatic space 14 formed between the elastic atrium 9, the rigid elements of housing 1 which confine the atrium, and the rigid septum 11, said carbon dioxide being under a pressure lower than that of the blood and preventing the irreversibility of embolism should a perforation take place in the elastic atrium 9. Two elastic tubes 15 and 16 made of polyurethane provide a seal between bucket 5 and cylinder 4, the space between the said tubes being filled with kerosene. The inner tube 15 is tightly fitted with its edge to the circumference of piston 6, the other edge being tightly fitted to the inner surface of cylinder 4. The outer tube 16 is tightly fitted with its edge to the circumference of the top part of housing 1, the other edge being tightly fitted over the outer surface of bucket 5. Valves 17 are installed in ports 2, 3 and 10 of the heart, said valves being made of two leaves forming a segment of a figure similar to a circle and pointing towards one another with their straight edges, said valves being attached to the walls of ports 2, 3 and 10 by means of circular edges. Each leaf consists of two layers 18 and 19 of materials of different elasticity, said material being in the described case the polyurethane material, each layer having a different degree of polymerization. The layer 18 of material of a higher elasticity is used at the side of blood inflow. The vaulted top part of housing 1 is connected with a branched shank 20 by which the heart is attached to the upper ribs of the person carrying the artificial heart. Both cylinders 6 are rigidly fixed to a bearing means comprising an elastic, branched, membranaceous and pedate bearer 21, said bearer being designed to rest with its membranaceous part 22 against the diaphragm of the person carrying the heart, on the principle of laminar suction, the pedate elements 23 of the said bearer being designed to be attached to the eleventh ribs. The inner faces of the heart which are in contact with blood are lined with a smooth layer of artificial endocardium made of materials of negative electric potential relative to a hydrogen electrode, while the outer faces of the said heart are lined with a smooth layer of artificial pericardium made of materials of zero electric potential relative to a hydrogen electrode.

The artificial heart of the invention operates on the principle of a biologically powered, hydraulic diaphragm-piston type pump. The motion of respiratory muscles of a person carrying the heart, particularly the motion of the diaphragm, provides the power for the heart, this power being transmitted via the branched bearer 21 to the buckets 5 sliding on cylinders 4.

In the compression phase, the convex piston 6 moves upward pressing the diaphragm 7, through the physiological liquid, against the elastic ventricle 8, said ventricle thus changing its shape from an ovoid to that of a flattened crescent and causing blood to flow out of ventricle 8 and out of the heart. The elastic atrium expands in this phase, the blood flows into the ventricle and valve 17 closes the port 10. Valve 17 in inlet port 2 is open, and valve 17 in outlet port 3 is also open. In the expansion phase, the piston 6 moves downward, the elastic diaphragm 7 returns to its previous position, the shape of ventricle 8 changes from that of a flattened crescent to the ovoid and fills up with blood flowing in from the atrium 9 via port 10 opened by valve 19. Atrium 9 contracts in this phase, valve 17 in the inlet port 2 opens while in the outlet port 3 valve 17 closes thus preventing return of the blood back to the ventricle 8.

What I claim is:

1. An artificial heart comprising a rigid housing including an upper portion having an inlet for blood, an elastic atrium mounted in said upper portion at said inlet, an elastic ventricle chamber in said housing capable of undergoing deformation between a deformed pressurized condition and a relaxed condition, said ventricle chamber being connected to said atrium for receiving blood therefrom, said housing having an outlet for blood, said ventricle chamber being connected to said outlet for discharge of blood therefrom, first valve means at said inlet for opening when said ventricle chamber is relaxed, second valve means between said atrium and said ventricle chamber for opening when said ventricle chamber is relaxed, and third valve means at said outlet for opening when the ventricle chamber is deformed, said housing including a lower portion surrounding said ventricle chamber, and actuator means operatively associated with said lower portion of the housing and with said ventricle chamber for periodically deforming and relaxing said ventricle chamber, said actuator means including bearing means for being coupled with the respiratory muscles and their bony lining of a user of the artificial heart, said housing including means for attachment with the upper ribs of the user such that the motion of the respiratory muscles of the user drives the actuator means and produces pumping action by deformation and relaxation of the ventricle chamber.

2. An artificial heart as claimed in claim 1 wherein the attachment means of the housing comprises a branched shank on said upper portion.

3. An artificial heart as claimed in claim 2 wherein said housing includes first and second portions containing a respective said atrium and ventricle chamber and having a respective said inlet and outlet, each said atrium and ventricle chamber forming a symmetrical portion of the artificial heart.

4. An artificial heart as claimed in claim 3 wherein said lower portion of the housing comprises a cylindrically shaped portion surrounding each respective ventricle chamber, said actuator means comprising a bucket member slidably mounted on each cylindrically shaped portion of the housing, and a convex element secured to each said bucket member for deforming a respective said ventricle chamber by slidable movement of the bucket member on each cylindrically shaped portion.

5. An artificial heart as claimed in claim 4 wherein said convex element forms a hollow closed space in said bucket member, said space being filled with carbon dioxide.

6. An artificial heart as claimed in claim 5 wherein said bearing means comprises a branched, elastic, membranaceous and pedate bearer restable against the respiratory muscles and their bony lining.

7. An artificial heart as claimed in claim 4 wherein said actuator means further comprises an elastic diaphragm secured to said housing above a respective said convex element and in contact with a respective said ventricle chamber.

8. An artificial heart as claimed in claim 7 wherein each said ventricle chamber has ports in registry with the respective said inlet and outlet, said housing including a rigid septum between each said ventricle chamber and atrium.

9. An artificial heart as claimed in claim 8 wherein each said diaphragm is circumferentially secured to its respective ventricle chamber and defines an enclosed space therewith with a physiological liquid in said space isotonic relative to blood and containing anti-thrombotic substances.

10. An artificial heart as claimed in claim 9 comprising means forming a closed space between each convex portion and its respective diaphragm filled with a liquid having a density and viscosity less than that of water.

11. An artificial heart as claimed in claim 9 wherein each said atrium has one end secured to said housing at a respective inlet for blood and an outlet secured to said septum at said port of the ventricle chamber for admission of blood therein, said housing and atrium forming a closed space containing carbon dioxide.

12. An artificial heart as claimed in claim 4 wherein the volume of the ventricle chambers and the atria is about four times larger than that of a live heart.

13. An artificial heart as claimed in claim 1 wherein each said valve means comprises a valve member with two leaves, each leaf being a segment of a circular figure and having a peripheral edge affixed around a respective opening and having straight edges facing one another for overlapping in closed condition, each leaf consisting of two layers of materials having different elasticity, the layer of higher elasticity facing the side of blood inflow.

14. An artificial heart as claimed in claim 4 comprising seal means between each bucket member and the respective cylindrically shaped portion, said seal means comprising inner and outer elastic tubes defining a space filled with a liquid of viscosity lower than that of water, said inner tube having one end circumferentially sealed to said convex member and an opposite end circumferentially sealed to said cylindrically shaped portion, said outer tube having one end circumferentially sealed to the upper portion of said housing and an opposite end circumferentially sealed to said bucket member.

15. An artificial heart as claimed in claim 1 wherein the heart has inner surfaces for contact with blood and a smooth layer of artificial endocardium having negative electric potential relative to a hydrogen electrode coating said inner surfaces.

16. An artificial heart as claimed in claim 1 wherein said heart has an outer surface and a smooth layer of artificial pericardium having zero electric potential relative to a hydrogen electrode coating said outer surface.

* * * * *